United States Patent
Haar

(10) Patent No.: US 8,298,159 B2
(45) Date of Patent: Oct. 30, 2012

(54) DISPOSABLE DIAGNOSTIC ARTICLE

(75) Inventor: Hans-Peter Haar, Wiesloch (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 416 days.

(21) Appl. No.: 12/570,458

(22) Filed: Sep. 30, 2009

(65) Prior Publication Data

US 2010/0049091 A1 Feb. 25, 2010

Related U.S. Application Data

(63) Continuation of application No. PCT/EP2008/053855, filed on Mar. 31, 2008.

(30) Foreign Application Priority Data

Apr. 4, 2007 (EP) .................... 07105656

(51) Int. Cl.
*A61B 5/00* (2006.01)
*B65D 81/00* (2006.01)
(52) U.S. Cl. ...................... 600/583; 600/573
(58) Field of Classification Search ............ 600/573, 600/583, 584; 606/181
See application file for complete search history.

(56) References Cited

U.S. PATENT DOCUMENTS

| | | |
|---|---|---|
| 5,217,480 A | 6/1993 | Haber et al. |
| 6,866,675 B2 | 3/2005 | Perez et al. |
| 2003/1001828 | 1/2003 | Effenhauser et al. |
| 2003/0149377 A1 | 8/2003 | Erickson et al. |
| 2004/1010694 | 5/2004 | Roe et al. |
| 2007/0016103 A1* | 1/2007 | Calasso et al. ............... 600/583 |
| 2008/0200887 A1 | 8/2008 | Haar et al. |
| 2008/0249435 A1 | 10/2008 | Haar et al. |
| 2009/0093695 A1 | 4/2009 | Nakamura et al. |
| 2009/0099477 A1 | 4/2009 | Hoenes et al. |

FOREIGN PATENT DOCUMENTS

| | | |
|---|---|---|
| EP | 1650560 A1 | 4/2006 |
| EP | 1759633 A1 | 3/2007 |
| JP | 2007040963 A | 2/2007 |
| WO | 2005084545 A1 | 9/2005 |
| WO | WO 2005/084530 A2 | 9/2005 |
| WO | WO 2005/084546 A2 | 9/2005 |

* cited by examiner

*Primary Examiner* — Jeffrey G Hoekstra
(74) *Attorney, Agent, or Firm* — Woodard, Emhardt, Moriarty, McNett & Henry LLP

(57) ABSTRACT

A disposable diagnostic article comprising a lancing element that can be pierced into a body part and a collection area formed on the lancing element for body fluid obtained by the puncture is disclosed. The lancing element can comprise at least two bent parts folded towards each other such that the at least two bent parts can partially delimit the collection area.

37 Claims, 4 Drawing Sheets

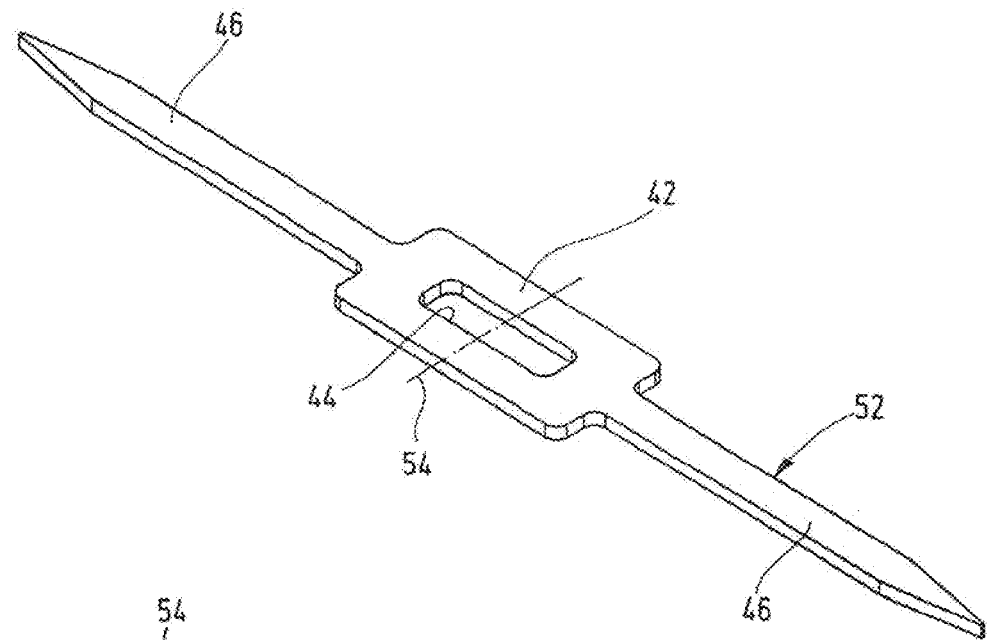
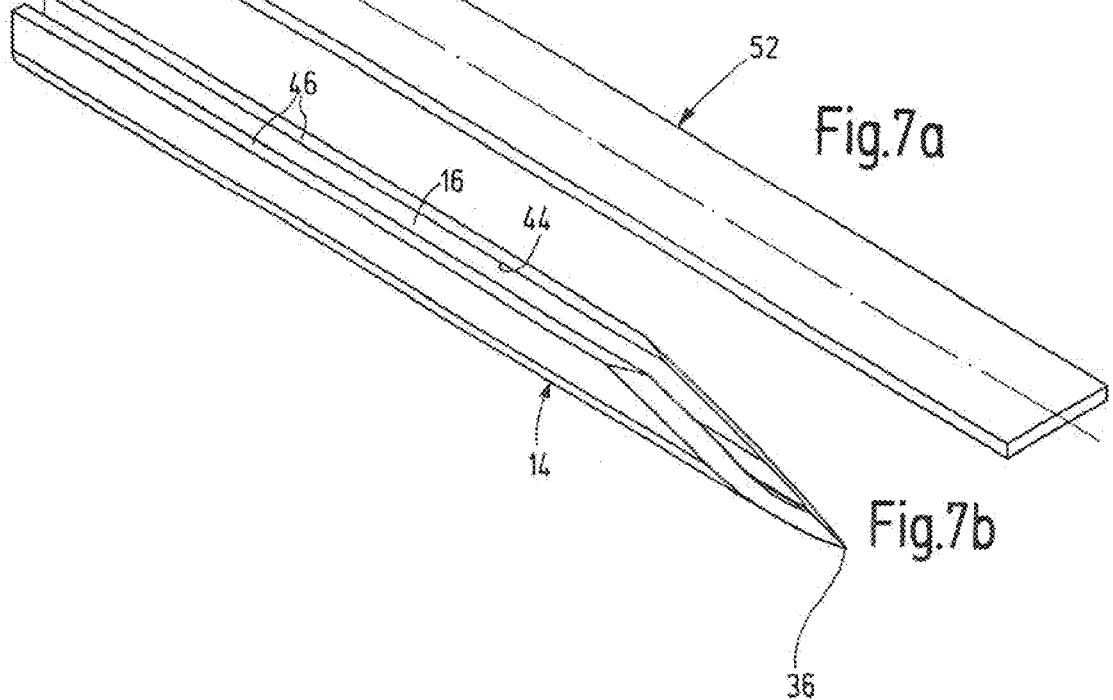

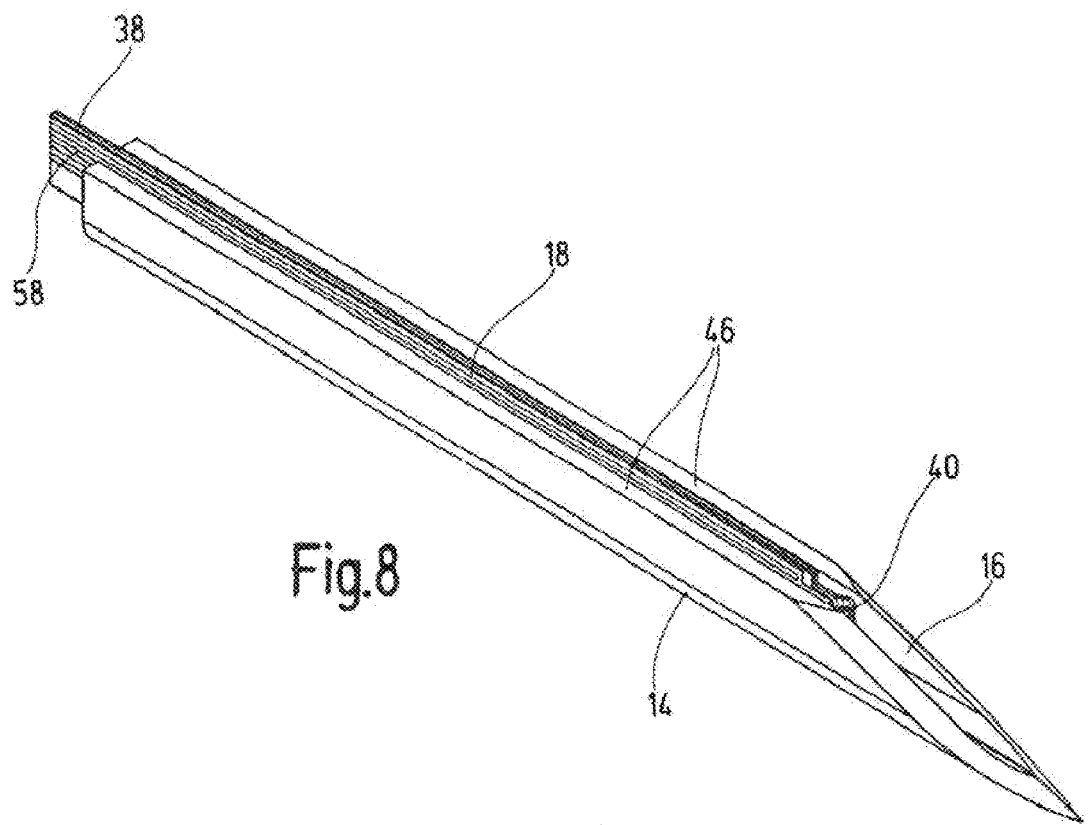
Fig.8
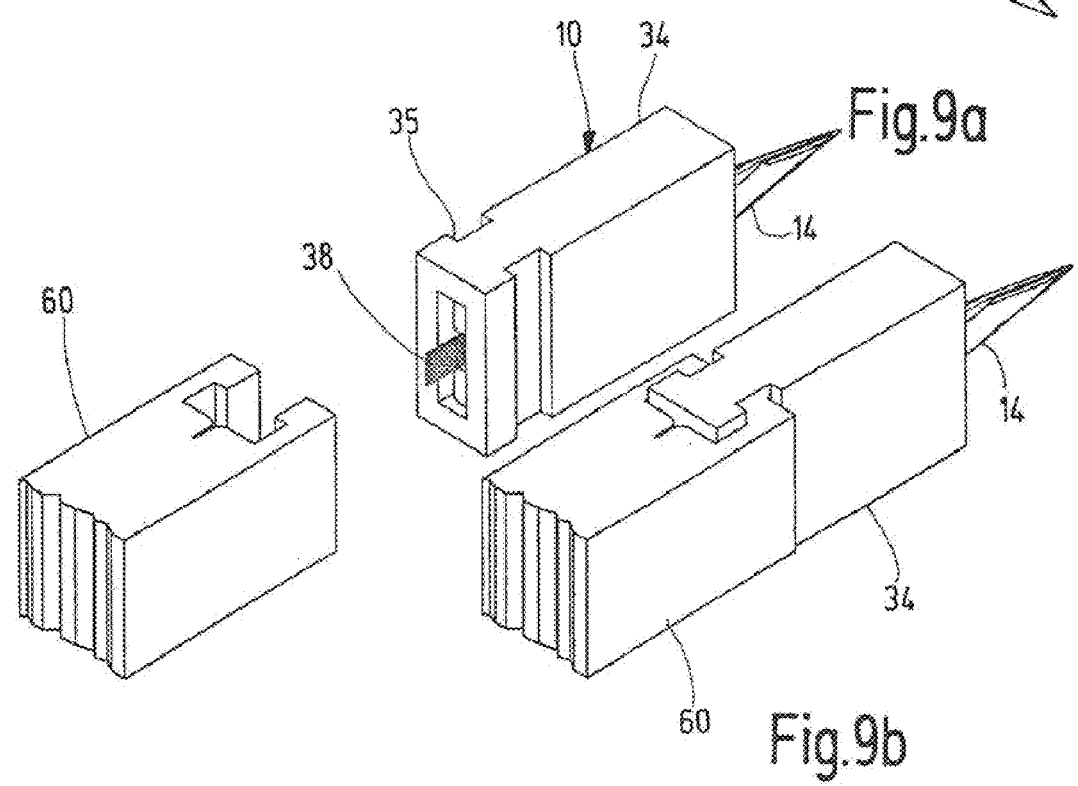
Fig.9a
Fig.9b

DISPOSABLE DIAGNOSTIC ARTICLE

CROSS-REFERENCE TO RELATED APPLICATIONS

This application is a continuation of International Application No. PCT/EP08/053,855, filed Mar. 31, 2008, which claims priority to EP 07 105 656.8, filed Apr. 4, 2007.

BACKGROUND

The present disclosure generally relates to a disposable diagnostic article for use in a microfluid collection unit for analyte testing in a body fluid sample and a method for fabricating such an article and, in particular, relates to a disposable diagnostic article for use in a microfluid collection unit for analyte testing in a body fluid sample, wherein the disposable diagnostic article comprises a lancing element to pierce a body part and a capillary-active collection area formed on the lancing element to collect body fluids obtained by the pierced body part and a method for fabricating such a microfluidic collecting unit.

In the case of typical blood sugar self-monitoring which usually has to be carried out by a diabetic several times daily as part of an insulin treatment, it is desirable to impose as few handling steps as necessary on the person concerned and, at the same time, it is desirable to ensure a reliable measurement with little pain. Disposable blood sugar testing articles are typically used for hygienic reasons. In general, it is preferable that the disposable blood sugar testing articles be produced at low cost as a mass-produced article.

Therefore, there is a need for body fluid self-monitoring systems, such as blood glucose testing systems, to be easy to operate with as little as pain as possible to the user and to have a simple and cost-effective design.

SUMMARY

According to the present disclosure, a disposable diagnostic article with a collection area formed on the disposable diagnostic article without complicated material processing steps is disclosed. The disposable diagnostic article can be designed for a single use. The disposable diagnostic article can comprise a lancing element. The lancing element can have at least two bent parts that can be folded towards each other such that the at least two bent parts can partially delimit the collection area. With regard to a production process, the collection area can be formed between the at least two bent parts that are bent towards one another by bend forming the lancing element.

The at least two bent parts that are folded towards one another can be simply joined together at a distance from the distal end and, in particular, can be spot-welded to thus achieve a substantially symmetrical shape relative to the lancing or longitudinal axis. Alternatively, it can also be possible that the bending zone can be formed by a bending edge running in the lancing direction of the lancing element so that the at least two bent parts can form a channel with a substantially U-shaped cross-section. In order to create a defined lancing structure, the ends of the at least two bent parts that form a lancing member can be joined together in a materially bonded manner.

In one exemplary embodiment, a test element can be inserted into the collection area through an opening on the lancing element near the proximal bending zone. The test element may be an electrochemical test strip as is known in the art.

The lancing element and the test element can be integrated into a carrier component housed within the diagnostic system. The carrier component can be coupled to an actuator which, in turn, can enable a reciprocating lancing movement along a lancing axis or direction.

Accordingly, it is a feature of the embodiments of the present disclosure to produce a diagnostic system that comprises a disposable diagnostic article that is easy to use and is cost-effective to produce. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which:

FIG. 6 illustrates a perspective view of a flat material blank for forming the lancing element as shown in FIGS. 4 and 5 according to an embodiment of the present disclosure.

FIG. 7 illustrates the lancing element in the initial state and end state according to an embodiment of the present disclosure.

FIG. 8 illustrates a perspective view of the lancing element as shown in FIG. 7 according to an embodiment of the present disclosure.

FIG. 9 illustrates a disposable diagnostic article with a lancing element and test element as shown as FIG. 8 according to an embodiment of the present disclosure.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

Figure 1:
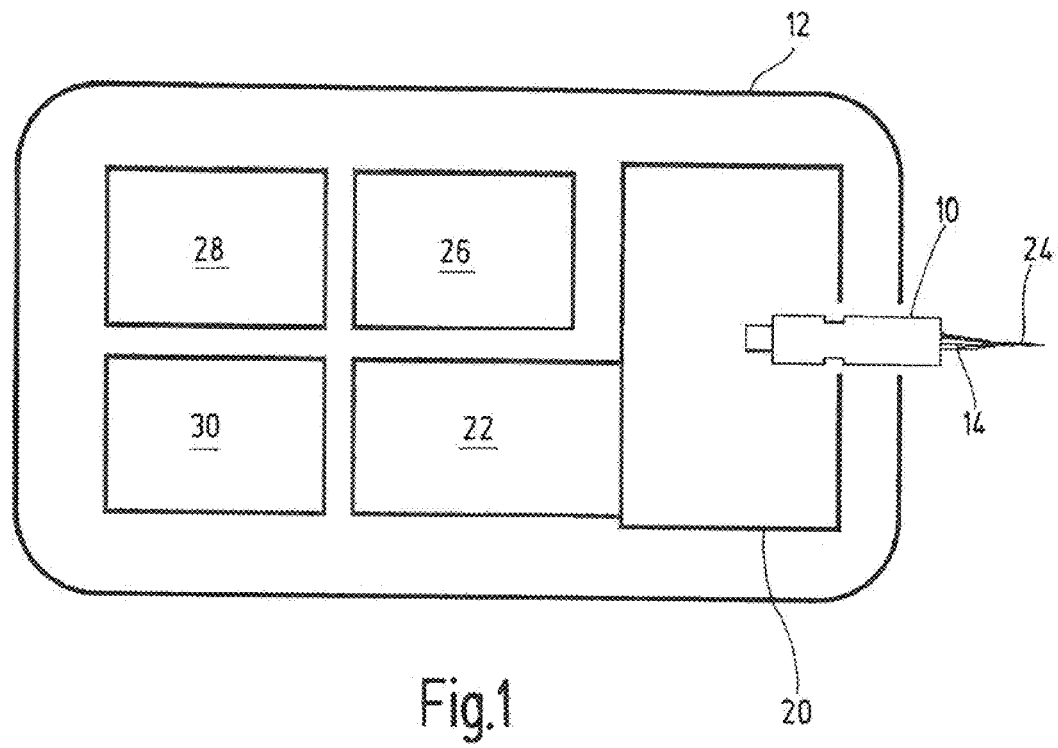
FIG. 1 illustrates a blood sugar measuring device with a disposable diagnostic article containing a lancing element according to an embodiment of the present disclosure.
Figure 2:
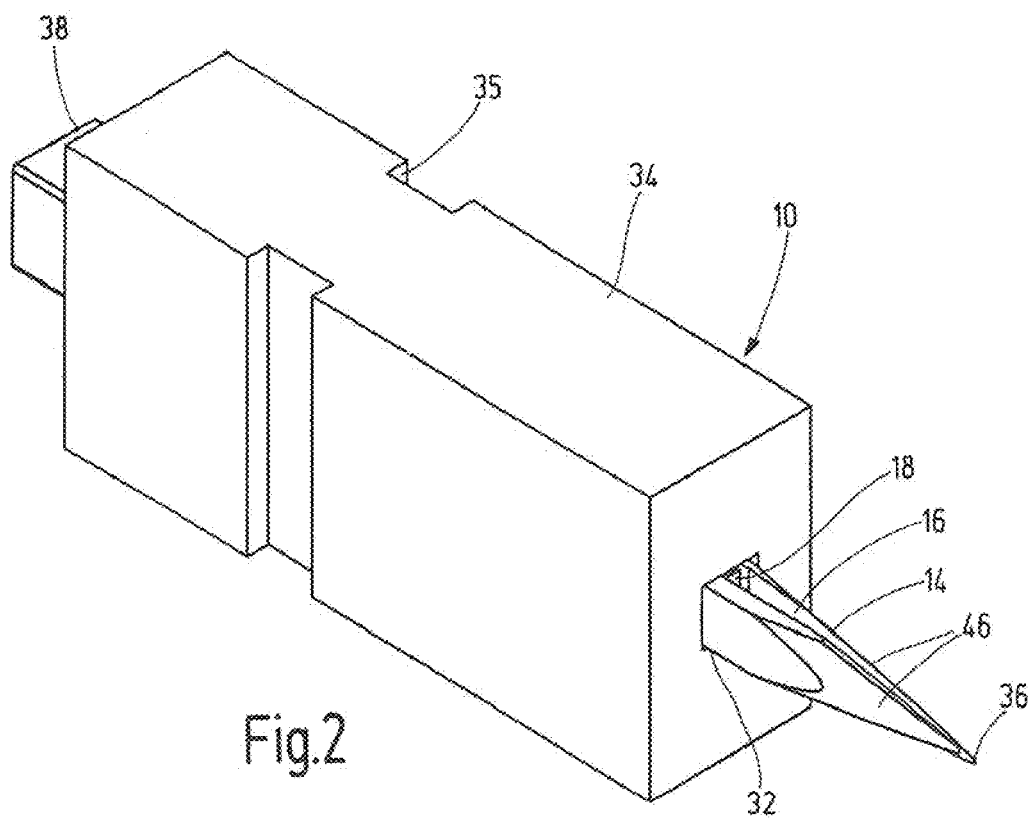
FIG. 2 illustrates a perspective view of the disposable diagnostic article as shown in FIG. 1 according to an embodiment of the present disclosure.

Referring initially to FIG. 1, an exemplary diagnostic system 12 comprising a housing, an actuator 22 located within the housing, and at least one disposable diagnostic article 10 is disclosed. Such diagnostic systems 12 can be used in the form of, for example, a portable hand-held device for determining an analyte in a body fluid sample, such as, for example, determining blood sugar. However, other types of near-patient monitoring known in the art, such as, for example, coagulation diagnostics, can be possible. In one exemplary embodiment, the disposable diagnostic article 10 can be a microfluidic collecting unit for use in a hand-held device 12 to measure blood sugar. In this exemplary embodiment, the disposable diagnostic article 10 can comprise a lancing element 14 that can be pierced into a body part in a lancing movement. Turning to FIG. 2, a collection area 16 for receiving a body fluid sample, such as, for example, a blood sample obtained by the puncture of a body part can be formed on the lancing element 14. The disposable diagnostic article may also comprise a test element 18 for detecting an analyte (e.g., glucose) in the body fluid sample. In another exemplary embodiment, the collected body fluid sample can also be transferred to a separate test element.

Turning back to FIG. 1, in one exemplary embodiment, the disposable diagnostic article 10 can be located in a magazine 20. The disposable diagnostic article 10 within the magazine 20 can be successively moved into an active position for use by an actuator 22. The actuator 22, which can engage the magazine 20, can enable a reciprocating lancing movement of the disposable diagnostic article 10 in a lancing axis or lancing direction 24. Returning to FIG. 2, measurement data can be obtained from the test element 18 and can be evaluated in an electronic processing unit 26. The evaluated measurement data can then be shown to the user via an output unit 28. In one exemplary embodiment, an energy supply 30 can enable independent operation of the diagnostic system 12 as a compact hand-held device so that the self-determination of an analyte in a body fluid sample, e.g., blood sugar concentration, can be reliably carried out in a substantially fully automatic measuring process, even by laymen, with a substantially high degree of handling convenience. In an exemplary embodiment, body fluid can also comprise body tissue, or mixtures thereof, which can also come into consideration as a sample in addition to body fluid, such as, for example, capillary blood from the skin.

In one exemplary embodiment, the lancing element 14 can be held in a holder 32 of a carrier component 34 in order to enable a drive coupling, for example via form-fitting notch 35, with the actuator 22. In one embodiment, a lancing member 36 of the disposable diagnostic article 10 can protrude in a distal direction from the carrier component 32. Additionally, a proximal protruding connecting component 38 of the test element 18 can enable a signal transfer of the measurement data from the test element 18 to the electronic processing unit 26. In one exemplary embodiment, the carrier component 34 can also be comprised of a plastic injection-molded part.

Figure 3:
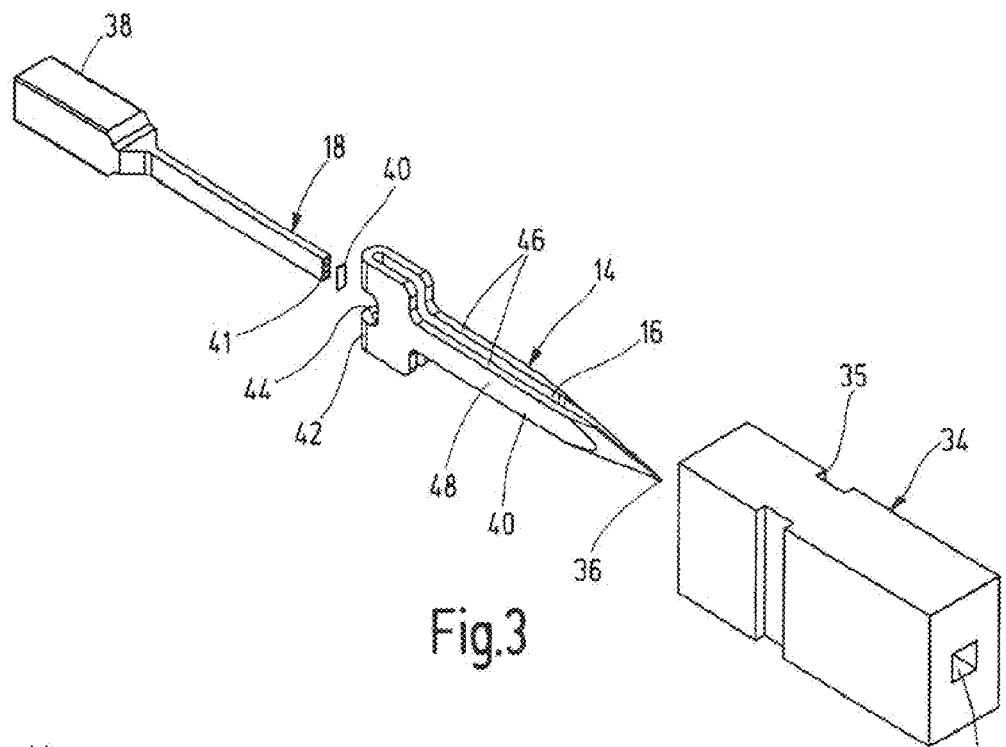
FIG. 3 illustrates an exploded view of the disposable diagnostic article as shown in FIG. 2 according to an embodiment of the present disclosure.

FIG. 3 illustrates one exemplary embodiment of how the individual components of the disposable diagnostic article 10 can be assembled. In one exemplary embodiment, the components can comprise the lancing element 14, the carrier component 34 and the test element 18. In one exemplary embodiment, the distal front face of the test element 18 can be provided with a reagent layer 40 that can respond to the analyte and can be connected via an optical signal conductor 41 with the connecting component 38 for a reflectometric measurement. In one exemplary embodiment, the reagent layer 40 can be in the form of a known enzymatic system which can irreversibly react with blood glucose resulting in a change in colour but does not dissolve in the blood fluid. In one exemplary embodiment, scattering particles within a chemistry system can scatter back the measuring light beamed in through the light guide 41 and thus can enable an optical detection by the diagnostic system.

In one embodiment, the shaft of the test element 18 with the reagent layer 40 coated front face can be inserted in the lancing direction into the proximal section of the collection area 16 such that the reagent layer 40 can substantially frontally delimits a body fluid flow cross-section. For this purpose, the lancing element 14 can have an opening 44 in the area of a proximal bending zone 42 which can open out into the collection area 16.

Figure 4:
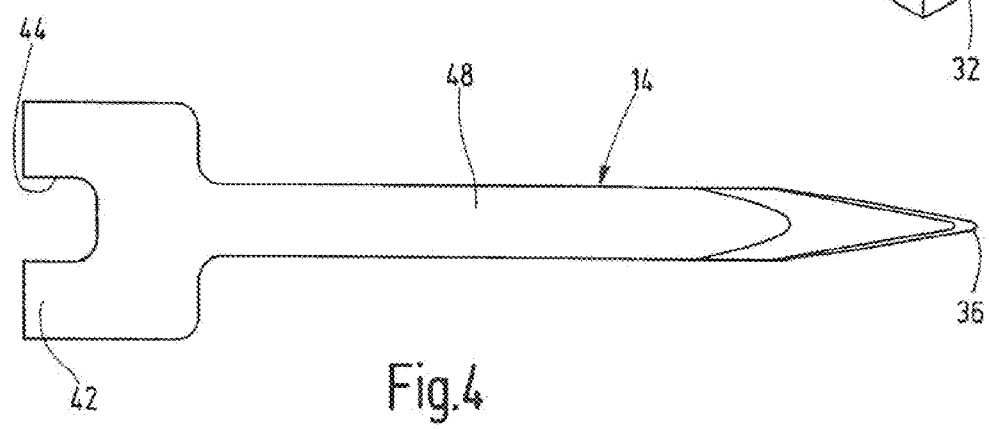
FIG. 4 illustrates a side view of a lancing element of the disposable diagnostic article formed by bending according to an embodiment of the present disclosure.
Figure 5:
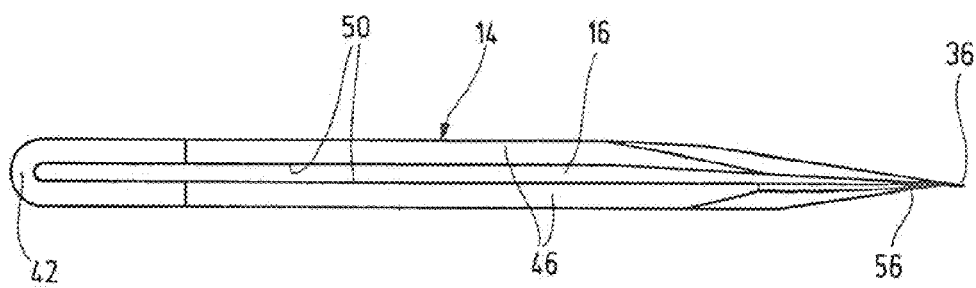
FIG. 5 illustrates another side view of a lancing element of the disposable diagnostic article formed by bending according to an embodiment of the present disclosure.

As shown in FIGS. 4 and 5, in one exemplary embodiment, the collection area 16 can be substantially delimited on both sides by at least two bent parts 46 of the lancing element 14 which can be bent or folded towards one another. Thereby, a geometrically delimited form of the lancing element 14 can be generated as a collecting volume without having to remove or cut any material. In one embodiment, only a minimal amount of body fluid, such as, for example, blood, needs to be taken up in the volume space that is formed solely by bending the lancing element 14 by capillary forces so that the user does not have to additionally monitor the sampling of the body fluid sample.

In one exemplary embodiment, the structure of the lancing element 14 can be very simply made by folding a flat workpiece. In this embodiment, the at least two bent parts 46 can have opposing limiting surfaces for the collection area 16. The at least two bent parts 46 can be joined together by a bending zone of the lancing element 14 which can be shaped by bending so that a uniform body can remain. The at least two bent parts 46, or bent members, can form a lancing shaft 48. In one exemplary embodiment, the distal end of the lancing shaft 48 can be ground to form a tip, a lancing member, 36. Thus, the capillary gap 30 can be kept free, or open, between the opposing limiting surfaces 50 of the bent parts 46 where the capillary gap 30 can be continuously open on the longitudinal edges pointing at substantially right angles to the lancing axis 24, in order to facilitate the entry of the body fluid. In another exemplary embodiment, the gap-shaped collection area 16 can be continuously on both sides. The capillary gap 30 can help ensure an effective uptake of body fluid without the risk of blockage by cell components. By avoiding dead spaces and longer transport paths, it can be possible to reduce the collection volume to a few tens of nanoliters which can enable a gentle and relatively painless blood collection.

As discussed above, in one exemplary embodiment, a further simplification can be achieved by forming the lancing element 14 from a single piece of flat material such as, for example, a sheet-metal blank 52 by bending as is illustrated in FIG. 6. In one exemplary embodiment, the metal blank 52 can be stainless steel sheet. However, any other suitable metal blanks known in the art can be used. In one exemplary process, the at least two symmetrical bent parts 46 can be bent around a bending line 54 extending from approximately the center and at substantially right angles to the lancing axis 24 where the bending angle can be about 90° in each case. In this exemplary embodiment, it may be advantageous for the production process to have the bending zone formed at the proximal end section of the lancing element 14 running at substantially right angles to the lancing direction or lancing axis 24.

In one exemplary embodiment, the ends of the at least two bent parts 46 that form the lancing element 14 can be joined together in a materially bonded manner. Subsequently, in one exemplary embodiment, the tips of the bent parts 46 can be joined permanently together by a welding spot 56. By spot-welding, a substantially symmetrical shape relative to the lancing or longitudinal axis can be achieved. In one exemplary embodiment, the tips of the bent parts 46 can be ground in such a manner that a sharp tip 36 can be formed. Thus, overall a diagnostic disposable article 10 can be manufactured from one workpiece by three simple processing steps, i.e., cutting, bending/folding and joining.

FIGS. 6-8 illustrate different configurations of the lancing element 14. Specifically, in FIG. 6, the bending line 54 can extend in the lancing direction approximately centrally through the flat material blank 52 so that the bent parts 46 can form a capillary channel with a substantially U-shaped cross-section. The substantially U-shaped cross-section can be formed in the bending zone by a bending edge running in the substantially lancing direction. A proximal section (i.e., facing away from the puncture site) of the collection area 16 can provide as a measuring zone at the same time. In this exemplary embodiment, a test element 18 designed to detect an analyte in the collected body fluid can be integrated as a further component. In order to simplify the production process, in one exemplary embodiment, it can be advantageous to have the test element 18 inserted into the lancing element 14 as a prefabricated insert. In another exemplary embodiment, the lancing element 14 can have an opening for inserting the test element 18 into the collection area 16 in particular in the area of the proximal bending zone. Accordingly, a proximal section of the collection area 16 can form a retainer for the test element 18. A prefabricated test element 18 can, in turn, be inserted in the collection area 16 that can be delimited in this manner. In one exemplary embodiment, as shown in FIG. 8, the test element 18 can be an electrochemical test strip. In this exemplary embodiment, a frontal reagent field 40 can be connected via electrical conductor paths 58 to the proximal connecting end 38. In another exemplary embodiment, the frontal reagent field 40 can be redundantly subdivided. In other words, the test element 18 can have a sensor area formed by a reagent layer 40, or an electrode, which can respond to the analyte in the body fluid and which can delimit a flow cross-section of the collection area 16 and can thus already be wetted by a microscopic volume of a flow front which flows against it.

In one exemplary embodiment, as shown in FIG. 9, the combined lancing and test element 14, 18 can be integrated into the carrier component 34. The carrier component 34 can be detachably drive coupled to a gripper 60 of the actuator 22 by the form-fitting notches 35 and, at the same time, the measurement data signal can be tapped at the connecting end 38. In one exemplary embodiment, the carrier component 34 can be designed to enable it to be stored, for example, in a stack magazine 20. In another exemplary embodiment, system integration can further be achieved by the test element 18 having at least one electrical, or optical signal conductor, such that, the signal conductor can be connected to measuring electronics 26 at a proximal contact section of the test element 18.

In another exemplary embodiment, automated handling can be further enhanced by having the lancing element 14 held in the carrier component 34 to move along for a forwards and backwards lancing movement 24. In this exemplary embodiment, as discussed above, the carrier component 34 can have a holder 32 for inserting the lancing element 14 and a coupling part for a drive coupling with the actuator 22.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

For the purposes of describing and defining the present disclosure, it is noted that the term "substantially" is utilized herein to represent the inherent degree of uncertainty that may be attributed to any quantitative comparison, value, measurement, or other representation. The term "substantially" is also utilized herein to represent the degree by which a quantitative representation may vary from a stated reference without resulting in a change in the basic function of the subject matter at issue.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A disposable diagnostic article for testing an analyte in a body fluid sample obtained from a body part, the article comprising:
 a lancing element for puncturing the body part, wherein the lancing element comprises;
  at least two bent parts folded towards each other, wherein the at least two bent parts are joined together at their ends to form a lancing member, and
  a bending zone shaped by the bending and joining of the at least two bent parts, wherein the at least two bent parts and the bending zone have a uniform cross-section, and
 a collection area formed on the lancing element for collecting body fluid obtained by a puncture, wherein the at least two bent parts at least partially delimit the collection area.

2. The disposable diagnostic article according to claim 1, wherein the collection area is a capillary gap between the at least two bent parts.

3. The disposable diagnostic article according to claim 1, wherein the collection area is continuously open on one side or continuously open on both sides along its longitudinal borders and pointing crosswise to a lancing direction.

4. The disposable diagnostic article according to the claim 1, wherein the at least two bent parts have opposing limiting surfaces for the collection area.

5. The disposable diagnostic article according claim 1, wherein the bending zone is formed at a proximal end of the lancing element.

6. The disposable diagnostic article according to claim 1, wherein the at least two bent parts are joined together by a welding spot.

7. The disposable diagnostic article according to claim 1, wherein the lancing element is formed by bending a single piece of flat material.

8. The disposable diagnostic article according to claim 7, wherein the single piece of flat material is a sheet-metal blank.

9. The disposable diagnostic article according to claim 1, further comprising,
 a test element to detect the analyte in the collected body fluid.

10. The disposable diagnostic article according to claim 9, wherein the test element is inserted into the lancing element as a prefabricated insert.

11. The disposable diagnostic article according to claim 9, wherein the lancing element comprises an opening for inserting the test element into the collection area.

12. The disposable diagnostic article according to claim 11, wherein the lancing element comprises an opening area in the proximal bending zone for inserting the test element into the collection area.

13. The disposable diagnostic article according to claim 9, further comprising,
   a proximal end of the collection area forms a retainer for the test element.

14. The disposable diagnostic article according to claim 9, wherein the test element comprises a sensor area formed by a reagent layer which responds to the analyte, wherein the sensor area delimits a flow cross-section of the collection area.

15. The disposable diagnostic article according to claim 9, wherein the test element has at least one optical signal conductor, wherein the at least one optical signal conductor is connected to measuring electronics at a proximal contact section of the test element.

16. The disposable diagnostic article according to claim 1, wherein the lancing element is held in a carrier component for a forwards and backwards lancing movement.

17. The disposable diagnostic article according to claim 16, wherein the carrier component comprises,
   a holder for inserting the lancing element, and
   a coupling part for a drive coupling.

18. The disposable diagnostic article according to claim 1, wherein the bending zone is formed between at least two bent parts, wherein the bending zone extends along a longitudinal length of the lancing element.

19. The disposable diagnostic article according to claim 1, wherein the bending zone extends transverse to a longitudinal length of the lancing element.

20. The disposable diagnostic article according to claim 1, further comprising:
   wherein the lancing element has a sharp tip; and
   wherein the collection area extends to the sharp tip of the lancing element; and
   wherein the sharp tip tapers to a point along the bending zone.

21. A disposable diagnostic article for testing an analyte in a body fluid sample obtained from a body part, the article comprising:
   a lancing element for puncturing the body part, wherein the lancing element comprises;
      at least two bent parts folded towards each other, wherein the at least two bent parts are joined together at their ends to form a lancing member, and
      a bending zone shaped by the bending and joining of the at least two bent parts, wherein the bending zone is formed between the at least two bent parts, wherein the bending zone extends along a longitudinal length of the lancing element, and
   a collection area formed on the lancing element for collecting body fluid obtained by a puncture, wherein the at least two bent parts at least partially delimit the collection area.

22. The disposable diagnostic article according to claim 21, wherein the collection area is a capillary gap between the at least two bent parts.

23. The disposable diagnostic article according to claim 21, wherein the collection area is continuously open on one side.

24. The disposable diagnostic article according to claim 21, wherein the lancing element is formed by bending a single piece of flat material.

25. The disposable diagnostic article according to claim 21, further comprising, a test element to detect the analyte in the collected body fluid.

26. The disposable diagnostic article according to claim 25, wherein the test element has at least one optical signal conductor, wherein the at least one optical signal conductor is connected to measuring electronics at a proximal contact section of the test element.

27. The disposable diagnostic article according to claim 21, wherein the lancing element is held in a carrier component for a forwards and backwards lancing movement.

28. The disposable diagnostic article according to claim 27, wherein the carrier component comprises,
   a holder for inserting the lancing element, and
   a coupling part for a drive coupling.

29. The disposable diagnostic article according to claim 21, further comprising:
   wherein the lancing element has a sharp tip; and
   wherein the collection area extends to the sharp tip of the lancing element; and
   wherein the sharp tip tapers to a point along the bending zone.

30. A disposable diagnostic article for testing an analyte in a body fluid sample obtained from a body part, the article comprising:
   a lancing element having a sharp tip for puncturing the body part, wherein the lancing element comprises;
      at least two bent parts folded towards each other, wherein the at least two bent parts are joined together at their ends to form a lancing member, and
      a bending zone shaped by the bending and joining of the at least two bent parts, and
   a collection area formed on the lancing element for collecting body fluid obtained by a puncture, wherein the at least two bent parts at least partially delimit the collection area, wherein the collection area extends to the sharp tip of the lancing element, wherein the sharp tip tapers to a point along the bend zone.

31. The disposable diagnostic article according to claim 30, wherein the collection area is a capillary gap between the at least two bent parts.

32. The disposable diagnostic article according to claim 30, wherein the collection area is continuously open on one side.

33. The disposable diagnostic article according to claim 30, wherein the lancing element is formed by bending a single piece of flat material.

34. The disposable diagnostic article according to claim 30, further comprising, a test element to detect the analyte in the collected body fluid.

35. The disposable diagnostic article according to claim 34, wherein the test element has at least one optical signal conductor, wherein the at least one optical signal conductor is connected to measuring electronics at a proximal contact section of the test element.

36. The disposable diagnostic article according to claim 30, wherein the lancing element is held in a carrier component for a forwards and backwards lancing movement.

37. The disposable diagnostic article according to claim 36, wherein the carrier component comprises,
   a holder for inserting the lancing element, and
   a coupling part for a drive coupling.

* * * * *